(12) United States Patent  (10) Patent No.: US 6,610,088 B1
Gabbay  (45) Date of Patent: Aug. 26, 2003

(54) BIOLOGICALLY COVERED HEART VALVE PROSTHESIS

(76) Inventor: Shlomo Gabbay, #1 Randall Dr., Short Hills, NJ (US) 07078

( * ) Notice: Subject to any disclaimer, the term of this patent is extended or adjusted under 35 U.S.C. 154(b) by 0 days.

(21) Appl. No.: 09/563,565

(22) Filed: May 3, 2000

(51) Int. Cl.[7] .................................................. A61F 2/24
(52) U.S. Cl. ...................... 623/2.38; 623/2.41; 623/2.13
(58) Field of Search ................................ 623/2.14, 2.13, 623/2.15, 2.16, 2.12, 2.38, 2.4, 2.41, 2.42

(56) References Cited

U.S. PATENT DOCUMENTS

| 3,739,402 | A | * | 6/1973 | Cooley et al. ........................ 3/1 |
| 4,084,268 | A | | 4/1978 | Ionescu et al. .................. 3/1.5 |
| 4,477,930 | A | | 10/1984 | Totten et al. ..................... 3/1.5 |
| 4,629,459 | A | | 12/1986 | Ionescu et al. |
| 4,759,758 | A | * | 7/1988 | Gabbay ........................... 623/2 |
| 5,549,665 | A | | 8/1996 | Vesely et al. ................... 623/2 |
| 5,713,950 | A | | 2/1998 | Cox |
| 5,855,602 | A | | 1/1999 | Angell ............. 623/2 |
| 5,861,028 | A | | 1/1999 | Angell ............. 623/2 |
| 5,935,163 | A | | 8/1999 | Gabbay ........................... 623/2 |
| 6,074,419 | A | | 6/2000 | Healy et al. |
| 6,102,944 | A | | 8/2000 | Huynh et al. |

* cited by examiner

Primary Examiner—Bruce Snow
(74) Attorney, Agent, or Firm—Tarolli, Sundheim, Covell & Tummino L.L.P.

(57) ABSTRACT

A system and method are disclosed for covering a heart valve prosthesis with biological tissue, such as pericardium. In one aspect, the prosthesis includes a stent that is covered with a fabric material. A heart valve is mounted within the stent, such as by sutures securing the heart valve to the fabric covering. One or more sheets of biological tissue are applied to the stented prosthesis so as to cover exposed areas of the fabric material.

13 Claims, 4 Drawing Sheets

BIOLOGICALLY COVERED HEART VALVE PROSTHESIS

TECHNICAL FIELD

The present invention relates to an implantable prosthetic device and, more particularly, to a system and method for providing a biologically covered heart valve prosthesis.

BACKGROUND

It is well known to utilize mechanical heart valves, such as the ball check valve, and natural tissue cardiac valves to replace defective aortic and mitral valves in human patients. One type of natural tissue heart valve typically employs a porcine valve for implantation in a human, as they are very similar to human valves of appropriate size and generally are easy to procure.

Prior art teaches the concept of removing an aortic heart valve from a pig, treating it with an appropriate fixation solution, which may include a glutaraldehyde solution, and mounting the valve into a stent.

A stent typically is formed of a resilient material, such as a plastic (e.g., DELRIN). Examples of various stent structures are disclosed in U.S. Pat. No. 3,983,581, U.S. Pat. No. 4,035,849. The stent usually is covered with a fabric material, such as DACRON or a suitable textile material. The fabric material provides structure for securing the valve relative to the stent. The stented heart valve prosthesis may be implanted into a patient for a heart valve replacement.

SUMMARY

The present invention relates to a system and method for covering a stented heart valve prosthesis with biological tissue, such as pericardium. The prosthesis includes a stent having a generally annular inflow end spaced from an outflow end. The stent is covered with a fabric material. A heart valve is mounted within the stent, such as by sutures securing the heart valve to the fabric covering. One or more sheets of the biological tissue is applied to the stented prosthesis so as to cover all exposed areas of the fabric material. As a result, there is a reduced likelihood of clot formation and a decreased likelihood that infection will occur after the prosthesis is implanted.

One aspect of the present invention provides a heart valve prosthesis that includes a stent having an annular base portion and a plurality of stent posts extending therefrom. The stent has a fabric covering. A natural tissue heart valve is mounted within said stent. At least one sheet of biological tissue covers all exposed fabric covering.

Another aspect of the present invention relates to a system for covering a fabric-covered stent with biological tissue. The stent has a plurality of stent posts extending in a first direction from an annular base portion of the stent. The stent has a fabric implantation flange extending radially from an exterior portion of the base portion, with the implantation flange having an inflow side and an outflow side. The system includes a pair of annular sheets of biological tissue dimensioned and configured for covering the inflow and outflow sides of the implantation flange in a sandwich-like manner. At least one additional sheet of pericardium covers a radially outer portion of each of the fabric-covered stent posts, whereby the fabric-covered exterior portions of the stent are completely covered with biological tissue.

Still another aspect of the present invention relates to a method for covering a heart valve prosthesis with biological tissue, the heart valve prosthesis including a stent having an annular base portion and a plurality of stent posts extending therefrom. A fabric material covers at least a radially exterior portion of the stent and a natural tissue heart valve is mounted within the fabric-covered stent. The method includes the step of covering all exposed fabric material with animal pericardium.

To the accomplishment of the foregoing and related ends, the invention, then, comprises the features hereinafter fully described and particularly pointed out in the claims. The following description and the annexed drawings set forth in detail certain illustrative aspects of the invention. These aspects are indicative, however, of but a few of the various ways in which the principles of the invention may be employed. Other objects, advantages and novel features of the invention will become apparent from the following detailed description of the invention when considered in conjunction with the drawings.

DESCRIPTION OF THE INVENTION

Figure 1:
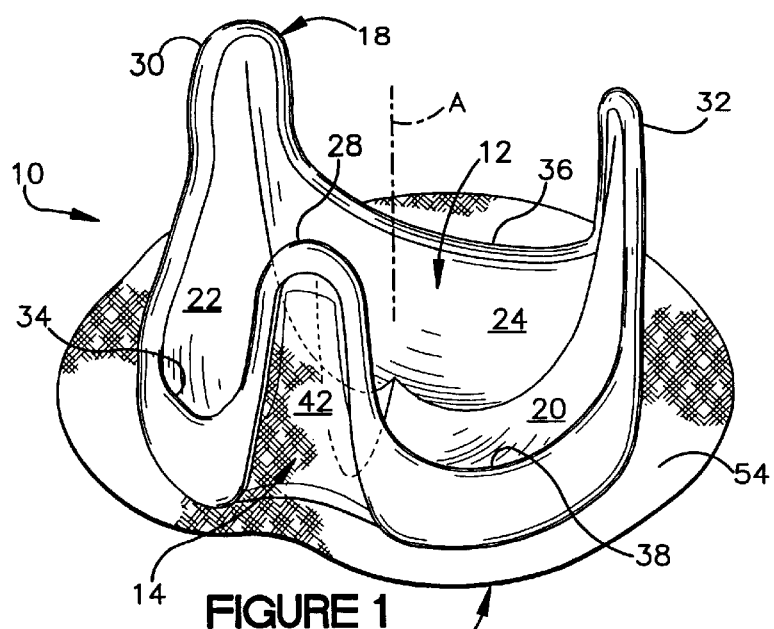
FIG. 1 is an isometric view of a heart valve mounted in a fabric-covered stent.

The present invention provides a system and method for covering a stented heart valve prosthesis and/or a stent with biological tissue, such as pericardium. The present invention will now be described with reference to the drawings, wherein like reference numerals are used to refer to like elements throughout.

FIG. 1 illustrates a stented heart valve 10, which may be employed to form a biologically covered heart valve prosthesis in accordance with the present invention. The stented heart valve 10 includes a heart valve 12 mounted or attached within in a conventional stent 14. The stented heart valve 10, for example, is of the type disclosed in U.S. Pat. No. 5,861,028 or U.S. Pat. No. 5,855,602, although other valve configurations also may be utilized without departing from the scope of the present invention.

By way of example, the valve 12 is a natural tissue heart valve, such as a porcine heart valve, which has been trimmed and fixed in an appropriate glutaraldehyde solution. An example of a suitable fixation environment is disclosed in U.S. Pat. No. 5,861,028. The valve 12 includes an inflow end 16, an outflow end 18 and a central axis, indicated at A, extending longitudinally through the inflow and outflow ends of the valve. The valve 12 also includes a plurality of leaflets or cusps 20, 22 and 24 mounted within a generally cylindrical sidewall portion 26 (see, e.g., cross sectional view of FIGS. 7 and 8), which may be a length of valve wall extending between the inflow and outflow ends 12 and 14. The sidewall portion includes circumferentially spaced apart commissures 28, 30, and 32, which form struts at the outflow end 16 near the juncture of adjacent pair of leaflets. The heart valve 10 also has sinuses 34, 36, and 38 formed in the outflow end 14 of the valve 10 between adjacent pairs of commissures 28 and 30, 30 and 32, 32 and 28, respectively.

Figure 2:
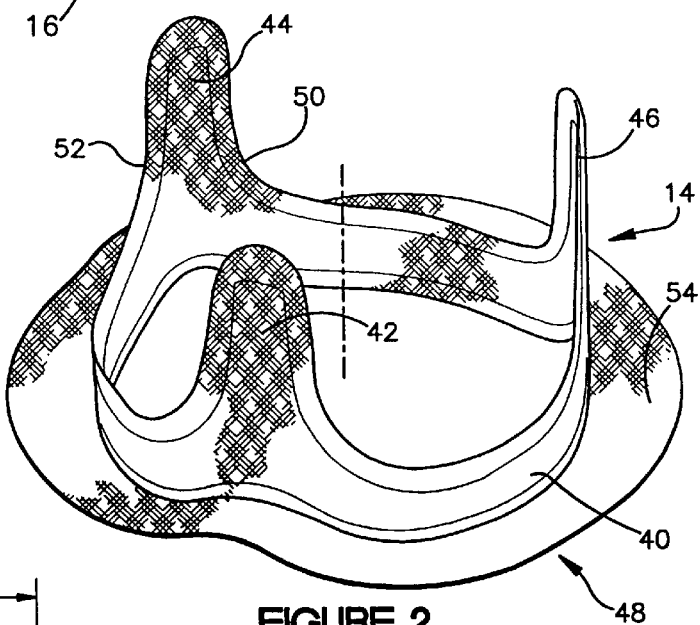
FIG. 2 is an isometric view of a fabric-covered stent.

FIG. 2 illustrates an example of the stent 14 illustrated in FIG. 1. The stent 14 includes an annular base portion 40 and elongated stent posts (or struts) 42, 44 and 46 extending from the annular base portion that correspond generally to the anatomical configuration of the heart valve 12. The stent posts 42, 44 and 46 are circumferentially spaced apart along an outflow end 50 of the base portion 40 to generally correspond to the radial positioning of the individual leaflets of the heart valve 12 (FIG. 1). The stent 14 also includes an inflow end 48 spaced axially from the outflow end 50.

The stent 14, for example, may be manufactured in various sizes and shapes by a conventional injection molding process. The stent 14 is typically formed of a thermoplastic material, such as the material known commercially as Delrin. The stent may be formed, however, of any other resilient, rigid, or flexible material according to the desired level of stiffness.

At least an exterior portion, although typically the entire stent structure 14 is covered with a nonabsorbent fabric material 52. The fabric covering is applied over and covers both the internal and external surfaces of the stent 22. By way of example, the fabric covering 52 may be an open mesh sheet of flexible material, such as a Dacron polymer cloth, a textile, or substantially equivalent material. It is to be appreciated that other fabric materials, such as plastics, synthetic materials, and the like also may be used. The fabric covering provides structure to which the valve 12 (FIG. 1) may be secured relative to the stent 14.

A generally annular implantation flange (or sewing ring) 54 may circumscribe the stent base 40 intermediate the inflow end 48 and the outflow end 50 of the stent 14. The flange 54, for example, is formed of the same material as the fabric covering 52. The flange 54 may be attached about the exterior of stent 14, such as by sewing the flange to the fabric covering 52 that surrounds the stent 14. Alternatively, the flange 54 may be formed from part of the fabric covering 52 that covers the stent 14 when the fabric covering is applied. The flange also may be ironed to form a substantially flat ring-like structure circumscribing the stent base 40. The particular positioning of the implantation flange 54 may depend upon whether the prosthesis 10 is to be implanted as a mitral valve or an aortic valve (See, e.g., U.S. Pat. No. 5,861,028). Examples of other types of stent structures that may be utilized include those disclosed in U.S. Pat. No. 3,983,581, U.S. Pat. No. 4,035,849, as well as any other stent structure known in the art.

Figure 3:
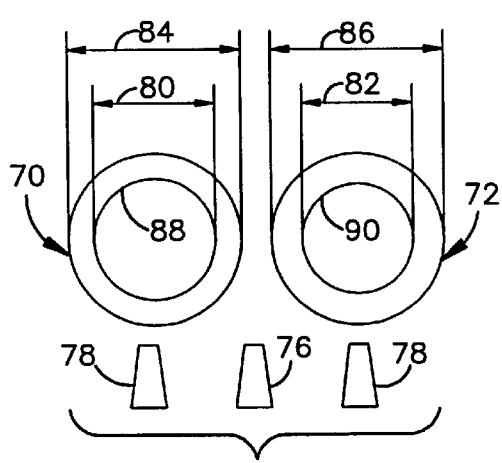
FIG. 3 is a plan view of sheets of biological material that may be employed to form a heart valve prosthesis in accordance with the present invention.

FIG. 3 illustrates a plurality of sheets 70, 72, 74, 76, and 78 of biological tissue that may be utilized, in accordance with an aspect of the present invention, to cover all fabric 52 that is exposed on a stented heart valve 12 (FIG. 1). The biological tissue, for example, is smooth animal pericardium (e.g., equine, bovine, porcine, etc.) that has been tanned or fixed in a suitable tanning environment. The tanned tissue also may be treated with heparin to improve its biocompatibility and mitigate thrombus formation.

Sheets 70 and 72 are in the form of generally annular rings, each having a respective inner diameter 80, 82 and outer diameter 84, 86. In particular, the ring 72 is dimensioned and configured for attachment to an inflow end of a stented valve 10 (FIG. 1) and, thus, has an inner diameter 82 that approximates the dimensions and configuration of the valve at the juncture between the valve and the fabric covering 52 located at the inflow end of the stented valve. The other ring 70 is dimensioned and configured to be attached to the outflow side of the implantation flange 54 (FIGS. 1 and 2). Each of the rings 70, 72 has a respective inner periphery 88, 90.

The remaining sheets 74–78 are in the form of patches that are dimensioned and configured to cover the remaining exposed fabric of the stented valve 10 (FIG. 1), namely, along the exterior of the stent posts 42–46 (FIGS. 1 and 2). While the patches are generally trapezoidal, it is to be understood and appreciated that other shapes may be used. For example, the shape of the patch may be selected according to the configuration of the stented valve and the contour of the exposed fabric material covering along the stent post and/or heart valve.

Figure 4:
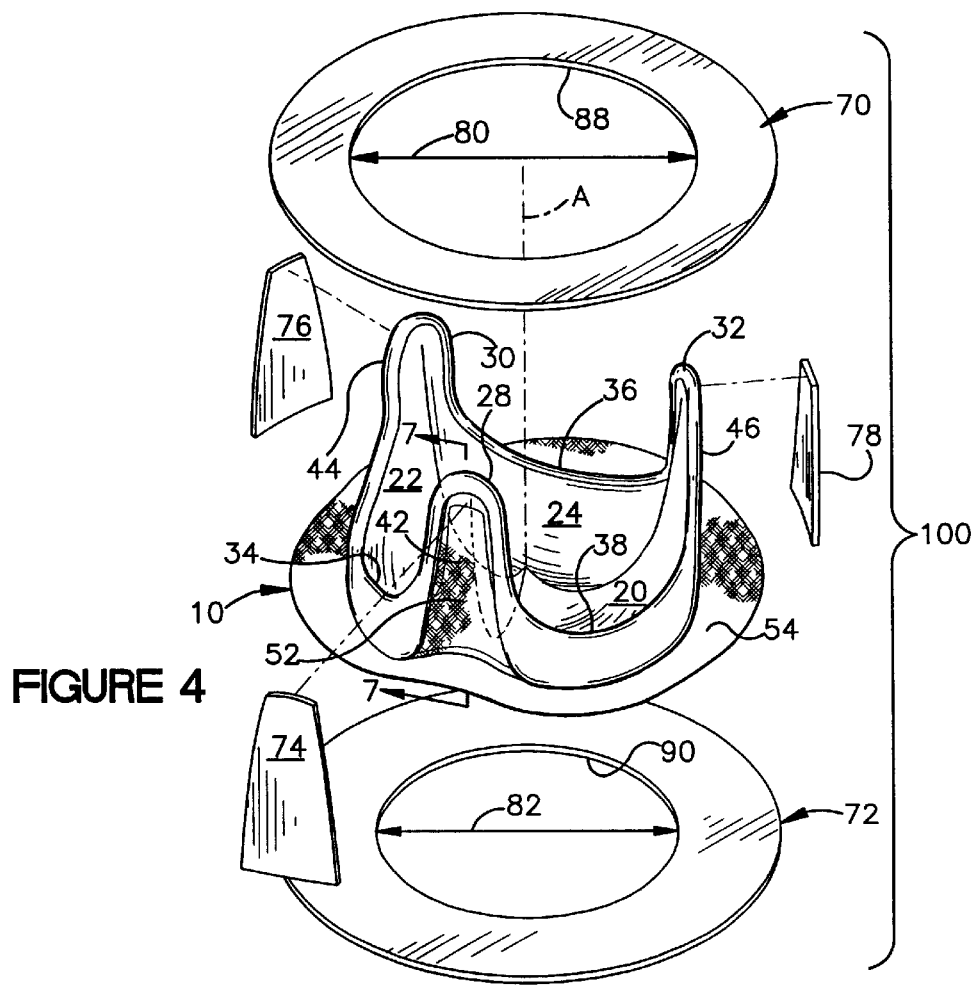
FIG. 4 is an exploded isometric view of a heart valve prosthesis in accordance with the present invention.

FIG. 4 is an exploded view of a heart valve prosthesis 100, in accordance with an aspect of the present invention, in which identical reference numbers are used to refer to parts previously identified with respect to FIGS. 1–3. The sheets of biological (e.g., pericardial) tissue 70–78 are aligned for attachment onto the stented valve 10, such that their visceral, or smooth, side is exposed. In particular, the ring 70 is oriented coaxially with axis A for attachment onto the inflow side of the implantation flange 54. As mentioned above, the inner diameter 80 of the ring 70 approximates (preferably slightly larger than) the outer diameter of the stented valve 10. As the ring 70 is mounted over the stent posts, the inner periphery 88 engages and circumscribes the stented valve 10 and is positioned at the juncture of the flange 54 and the stent base portion 40.

Similarly, the other ring 72 is aligned coaxially with axis A for attachment at the inflow end 16 of the stented valve 10. The inner diameter 82 is less than the outer diameter of the stented valve 10 at the inflow side juncture of the implantation flange 54 and the stent. As mentioned above, the inner diameter 82 of the ring 72 approximates the configuration of the inflow annulus of the valve 12 at the juncture of the valve and the fabric covering the stent 14. As a result, the ring 72 is able to completely cover all exposed fabric 52 at the inflow side, including the inflow side of the implantation flange 54.

The patches 74, 76, and 78 are aligned for attachment to cover exposed fabric 52 associated with each of the stent posts 42, 44, and 46, respectively. Once all the sheets are attached to the stented valve 10, no fabric material 52 is exposed. As a result, when the prosthesis 100 is implanted, there is no contact between blood and the fabric covering 52. This mitigates clot formation and infection which otherwise might occur in response to contact between blood and the fabric covering.

Figure 5:
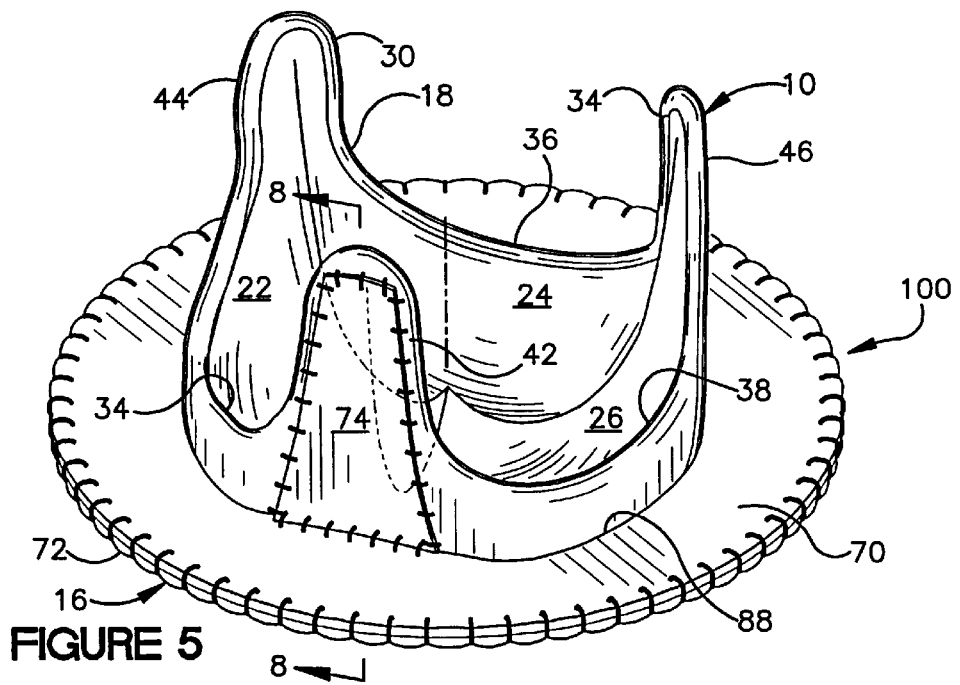
FIG. 5 is an isometric view of an inflow side of heart valve prosthesis in accordance with the present invention.
Figure 6:
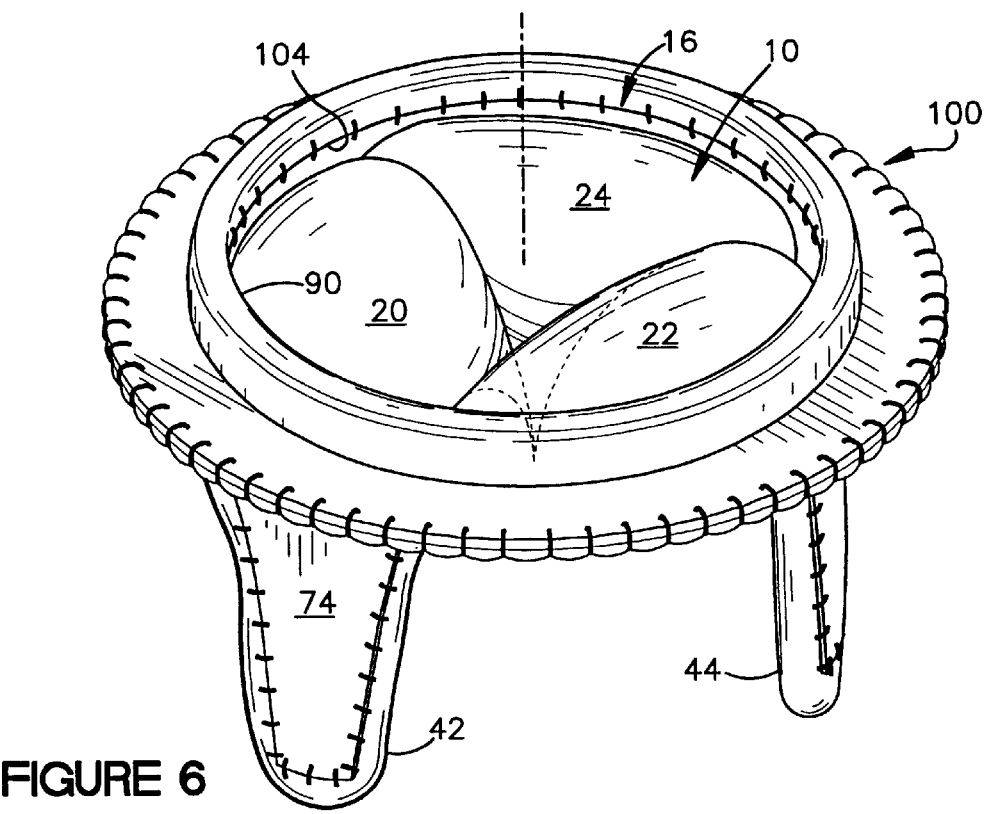
FIG. 6 is an isometric view of an outflow side of a heart valve prosthesis in accordance with the present invention.

FIGS. 5 and 6 illustrate the completed heart valve prosthesis 100 in which all exposed fabric material has been covered with biological tissue in accordance with an aspect of the present invention. In particular, FIG. 5 illustrates the prosthesis 100 as viewed from its outflow end. Each of the patches 74, 76, 78 (only patch 74 is shown) is sewn to the fabric material covering a radially outer portion of each respective stent post 42, 44, 46. The ring 70 engages and is connected to an outflow side of the implantation flange and the ring 72 engages and is connected to an inflow side of the implantation flange. The rings 70 and 72 are sewn together at an outer periphery thereof, thereby "sandwiching" the flange located between the rings. In addition or alternatively, the rings may be sewn to a perimeter to a portion of the implantation flange 54.

The inner periphery 88 of the ring 70 also is sewn to an adjacent part of the patches covering the radially outer portions the stent posts. Additional sutures (not shown) also may be employed to connect the inner periphery 88 to an outer portion of stent 14 between stent posts.

FIG. 6 illustrates the inflow end of the prosthesis 100 in which the ring 72 completely covers the fabric at the inflow end 16 of the prosthesis. The ring 72 is sewn at an inflow annulus 104 of the prosthesis 100 at the juncture of the valve 12 and the fabric-covered stent. Advantageously, the ring 72 of biological tissue conforms to the contour of at the inflow end, although additional sutures may be employed to ensure substantially tight engagement between the ring 72 and the stented heart valve 10.

Figure 7:
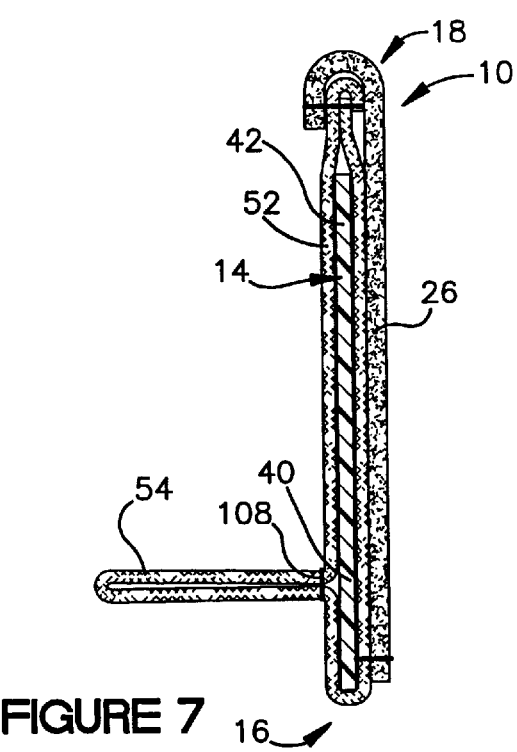
FIG. 7 is a partial side-sectional view of a stented heart valve taken along line 7—7 of FIG. 4.
Figure 8:
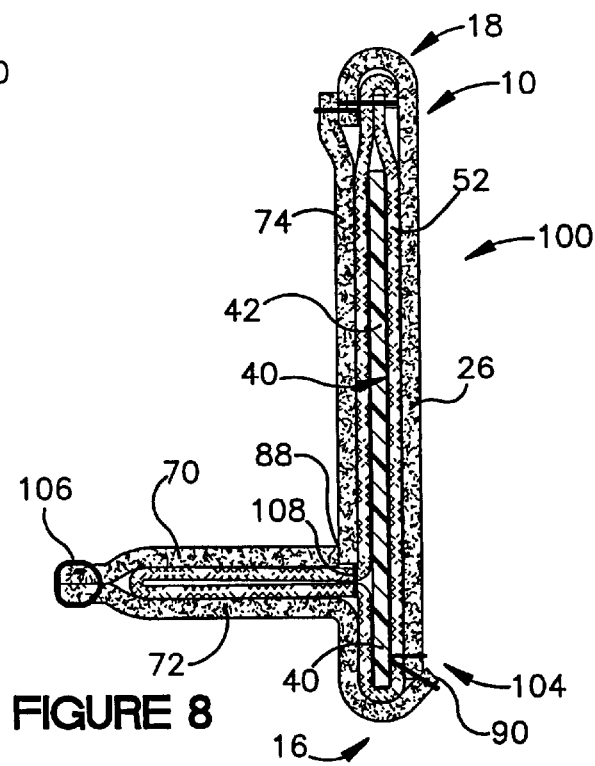
FIG. 8 is a partial side sectional view of a stented heart valve taken along line 8—8 of FIG. 5.

FIGS. 7 and 8 are cross-sectional views of part of valve structures shown and described herein. It is to be appreciated that the dimensions and relative position of corresponding parts has been exaggerated for purposes of clarity of illustration.

Referring to FIG. 7, a cross-sectional view of part of the stented heart valve of FIG. 4, taken along line 7—7, is illustrated. This further illustrates the fabric covering 52 that surrounds the stent 14. In addition, the implantation flange 54 is illustrated as being spaced from the inflow end 16 of the valve 10. A suture 108 may be employed to maintain the flange in a desire substantially flat configuration. As mentioned above, the relative axial placement of the implantation flange 54 on the stent 14 may vary according to whether the prosthesis is to be used for mitral or atrioventricular valve replacement, and all such positions are within the scope of the present invention. Moreover, the system and method, in accordance with an aspect of the present invention, also may be employed with a stent or stented valve having no implantation flange.

FIG. 8 is another cross-sectional view of part of the heart valve prosthesis 100 of FIG. 5, taken along line 8—8, in accordance with an aspect of the present invention. The rings 70 and 72 sandwich the implantation flange 54 and are connected together along the periphery of the rings and flange by appropriate sutures 106. As mentioned above, the sutures 106 alternatively may connect the rings 70 and 72 to the flange 54. The inner periphery 88, 90 of each ring 70, 72 also is sewn to a corresponding portion of the stented valve 10. In particular, the inner periphery 88 of the ring 70 is sewn to the patches (e.g., 74) and also may be connected to the underlying fabric covering 54 circumscribing the stented valve 10. The inner periphery of the ring 72 is sewn to the inflow annulus 104 of the prosthesis 100 so as to cover all fabric covering at the inflow portion of the stented valve. The biological tissue patch 74 also is sewn to cover the exposed portion of the fabric material associated with the stent post 42 (see, e.g., FIG. 5).

Figure 9:
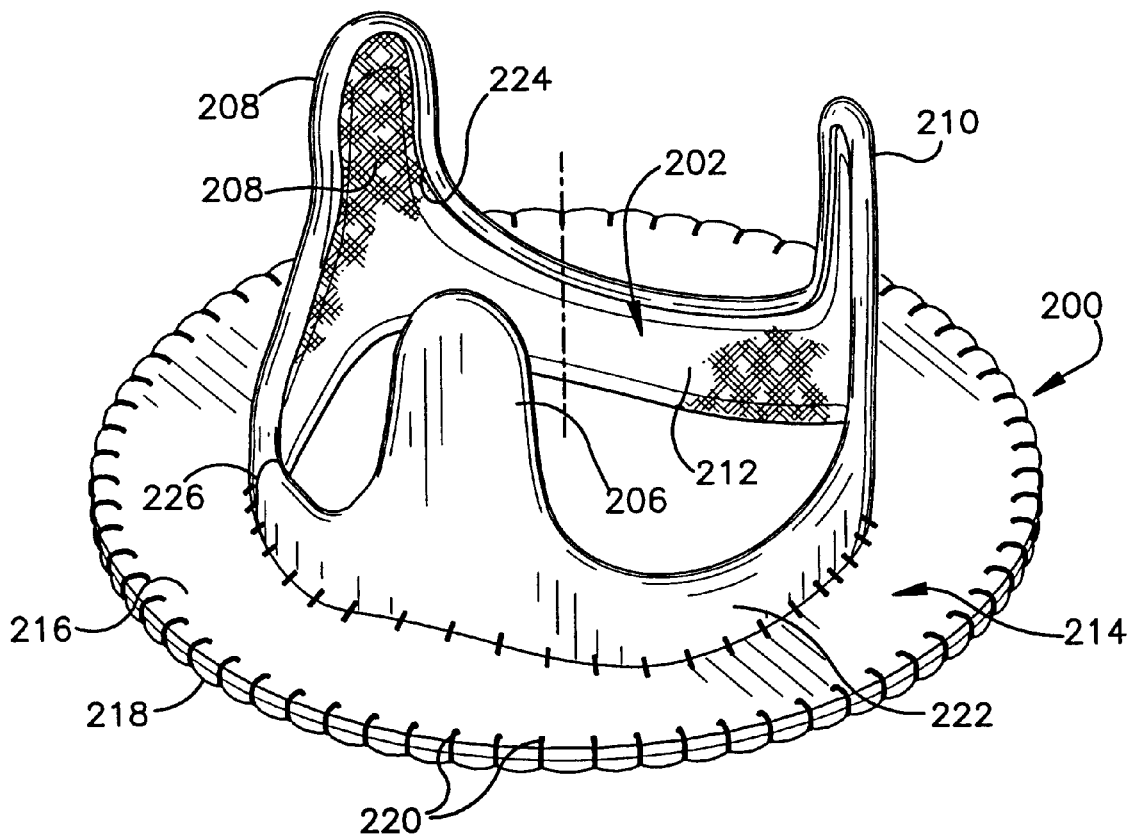
FIG. 9 is an isometric view of fabric-covered stent that is covered with biological tissue material in accordance with the present invention.

FIG. 9 is an example of a stent 200 that has been covered with biological tissue in accordance with an aspect of the present invention. The stent 200 includes a stent member 202 that has been covered with a fabric material 204, such as shown and described with respect to FIG. 2. The stent 200 also includes stent posts 206, 208, and 210 extending substantially coaxially from a stent base portion 212 in a circumferentially spaced apart relationship.

Biological material has been applied to a the fabric-covered stent member 202 in accordance with an aspect of the present invention. In particular, the stent 200 includes an implantation flange 214 formed of a two layers 216 and 218 of biological tissue (e.g., animal pericardium). Each of the layers 216, 218, for example, is in the form of a ring-like sheet of animal pericardium, such as sheets 70 and 72 shown and described hereinabove. The outer periphery of each of the layer is sewn together via sutures 220. The radially inner portion of each of the layers 216, 218 also is sewn the fabric covering 204.

A layer 222 of biological tissue also covers the fabric material 204 covering the radially outer extent of the stent 200. This layer 222 may be in the form of a single sheet of animal pericardium that circumscribes the fabric-covered stent 200. As illustrated in the example of FIG. 9, the layer 222 may be trimmed to conform to the contour of the stent posts 206–210 along a outflow end of the stent. The layer also may cover the fabric material 204 at an outflow margin 224 of the stent member 202 so as to mitigate abrasion that may occur upon contact between leaflets and the outflow rails. Because the layer 220 typically is formed of an elongated sheet of the biological tissue, a butt seam 226 is exposed. The butt seam 226 of the sheet 222 may be positioned intermediate stent posts 206 and 208, with two ends of the layer 222 seamed together end-to-end with substantially no overlap to define the seam.

It is to be appreciated that the layer 220 may be applied to the stent 200 before or after formation of the implantation flange 214. For example, if the stent 200 does not include a fabric implantation flange (as shown in FIG. 2), then the layer 220 may cover the entire radially outer portion of the stent member 202. A double layer (layers 216 and 218) biological material may then be configured to form the implantation flange 214, with the inner portion of each layer 210, 212 being secured to the stent outer layer 222 and/or to the underlying fabric covering 204. In contrast, if the stent 200 includes a fabric implantation flange, then the layer 222 may circumscribe an outflow portion of the stent 200, such as from the juncture of the flange to the outflow end of the stent 200.

While in the example of FIG. 9, the radially inner portion of the stent exposes some fabric material 214 (other than at the outflow margin 224), it is to be appreciated that the inner portion also may be covered with a biological material, such as animal pericardium. However, a heart valve mounted within the stent 200 usually will completely cover the interior exposed portions of the fabric material.

In view of the foregoing structure and methodology, it will be appreciated by those skilled in the art that a system and method according to the present invention help reduce a possible source of infection after the valve is implanted, namely, the fabric material that is exposed to blood. Once infection mounts in the fabric material, it is practically impossible to eradicate. As a result, the patient may require reoperation, which exposes the patient to additional risk that has a relatively high mortality rate. The fabric covering, if left exposed to blood, also provides a site that is prone to clot formation, which may result in other complications for the patient. A system and method in accordance with the present invention provides a heart valve prosthesis that mitigates clot formation as well as helps reduce the incidence of infection. The biological material covering also tends to improve the compatibility between the heart valve prosthesis and the valve recipient.

What has been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A heart valve prosthesis comprising:
   a stent having an annular base portion and a plurality of stent posts extending therefrom, the stent having a fabric covering;
   heart valve mounted within the stent to define a stented valve having exteriorized fabric covering;
   at least one sheet of biological tissue covering the exteriorized fabric covering of the stented valve; and
   a fabric implantation flange extending radially from the stent base portion, the at least one sheet of biological tissue covering the fabric implantation flange, whereby no fabric covering remains exposed.

2. A heart valve prosthesis as set forth in claim 1, wherein the implantation flange has inflow and outflow sides, the at least one sheet of biological tissue including a pair of annular sheets of biological tissue which respectively cover the inflow and outflow sides of the implantation flange.

3. A heart valve prosthesis as set forth in claim 2, wherein the annular sheet of biological tissue covering the outflow side of the implantation flange has an inner diameter that approximates an outer diameter of the fabric-covered stent near the outflow side of the implantation flange.

4. A heart valve prosthesis as set forth in claim 3, wherein the annular sheet of biological tissue covering the inflow side of the implantation flange has an inner diameter commensurate with a diameter associated with an inflow annulus at the juncture between the heart valve and the fabric-covered stent.

5. A heart valve prosthesis as set forth in claim 2, wherein the stent posts include an exterior portion, the at least one sheet of biological tissue further including a plurality of patches, each of the patches being dimensioned and configured to cover exposed fabric on the exterior portion of a respective one of the stent posts.

6. A heart valve prosthesis as set forth in claim 1, wherein the biological tissue further comprises animal pericardium.

7. A heart valve prosthesis as set forth in claim 6, wherein the animal pericardium comprises at least one of porcine pericardium, bovine pericardium, and equine pericardium.

8. A heart valve prosthesis, comprising:
   a support having an inflow annulus and an outflow end;
   a valve supported within an interior portion of the support to facilitate a substantially unidirectional flow of blood through the prosthesis;
   fabric material that extends around at least a portion of the support and around the valve, the fabric material further comprises an implantation flange that extends around the support at a location spaced from the outflow end, the at least one sheet of biological material covering the implantation flange; and
   at least one sheet of biological material around the valve and the stent to cover exposed portions of the fabric material.

9. The heart valve prosthesis of claim 8, wherein the at least one sheet of biological tissue further covers the inflow annulus.

10. The heart valve prosthesis of claim 8, wherein the implantation flange has inflow and outflow sides, the at least one sheet of biological tissue including a pair of annular sheets of biological tissue that respectively cover the inflow and outflow sides of the implantation flange.

11. The heart valve prosthesis of claim 10, wherein the annular sheet that covers the inflow side of the implantation flange has an inner diameter substantially commensurate with a diameter associated with an inflow annulus at the juncture between the heart valve and the fabric-covered stent, such that the annular sheet that covers the inflow side of the implantation flange also covers the inflow annulus of the support.

12. The heart valve prosthesis of claim 8, wherein the valve further comprises a natural tissue heart valve having leaflets that are moveable between open and closed conditions to facilitate substantially unidirectional flow of blood through the prosthesis.

13. The heart valve prosthesis of claim 8, wherein the support further comprises a stent in which the natural tissue heart valve is mounted.

* * * * *